United States Patent
Chen et al.

(10) Patent No.: US 12,281,348 B2
(45) Date of Patent: Apr. 22, 2025

(54) METHOD FOR THE CONTINUOUS FLOW SYNTHESIS OF (R)-4-HALO-3-HYDROXY-BUTYRATE

(71) Applicant: Fudan University, Shanghai (CN)

(72) Inventors: Fener Chen, Shanghai (CN); Dang Cheng, Shanghai (CN); Zedu Huang, Shanghai (CN); Minjie Liu, Shanghai (CN); Huashan Huang, Shanghai (CN); Meifen Jiang, Shanghai (CN); Lulu Wang, Shanghai (CN)

(73) Assignee: Fudan University, Shanghai (CN)

( * ) Notice: Subject to any disclaimer, the term of this patent is extended or adjusted under 35 U.S.C. 154(b) by 611 days.

(21) Appl. No.: 17/516,894

(22) Filed: Nov. 2, 2021

(65) Prior Publication Data

US 2022/0056489 A1 Feb. 24, 2022

(30) Foreign Application Priority Data

Nov. 8, 2020 (CN) .......................... 202011235128.8

(51) Int. Cl.
*C12M 1/00* (2006.01)
*C12M 1/02* (2006.01)
(Continued)

(52) U.S. Cl.
CPC ............. *C12P 7/625* (2013.01); *C12M 23/58* (2013.01); *C12M 27/00* (2013.01); *C12M 29/00* (2013.01);
(Continued)

(58) Field of Classification Search
CPC ........ C12P 7/625; C12M 23/58; C12M 27/00; C12M 29/00; C12M 41/12; C12M 41/26;
(Continued)

(56) References Cited

U.S. PATENT DOCUMENTS 4,710,468 A 12/1987 Sih

FOREIGN PATENT DOCUMENTS

| CN | 101224405 A | 7/2008 |
| CN | 103182277 A | 7/2013 |

(Continued)

OTHER PUBLICATIONS

Jensen, K. Flow chemistry—Microreaction technology comes of age, 2018, AIChE Journal, 63(3): 858-869 (Year: 2018).*

(Continued)

*Primary Examiner* — Louise W Humphrey
*Assistant Examiner* — Anjali Ajit Hirani

(57) ABSTRACT

This application relates to organic synthesis, and more particularly to a method for the continuous flow synthesis of (R)-4-halo-3-hydroxy-butyrate using a micro-reaction system. This application performs an enzymatic asymmetric reduction of a substrate solution containing halogenated acetoacetate and a biocatalyst solution in the micro-reaction system composed of a micro-mixer, a micro-channel reactor, and a pH regulator to obtain the (R)-4-halo-3-hydroxy-butyrate. Compared to the prior art, the reaction time of the method is only a few minutes, the yield of the product (R)-4-halo-3-hydroxy-butyrate is greater than 95%, the reaction process is continuous, the degree of automation is high, the efficiency is high, and the process is simple to operate and easy to be used in industrialized production.

10 Claims, 2 Drawing Sheets
Specification includes a Sequence Listing.

(51) Int. Cl.
*C12M 1/34* (2006.01)
*C12M 1/36* (2006.01)
*C12P 7/625* (2022.01)

(52) U.S. Cl.
CPC ............ *C12M 41/12* (2013.01); *C12M 41/26* (2013.01); *C12M 41/48* (2013.01); *C12Y 101/01184* (2013.01)

(58) Field of Classification Search
CPC .................. C12M 21/18; C12M 23/16; C12Y 101/01184; B01F 33/30; B01J 19/0093
See application file for complete search history.

(56) References Cited

FOREIGN PATENT DOCUMENTS

| | | | |
|---|---|---|---|
| CN | 106947752 | A | 7/2017 |
| CN | 108018321 | A | 5/2018 |
| CN | 110862320 | A | 3/2020 |
| CN | 111172124 | A | 5/2020 |
| CN | 111269099 | A | 6/2020 |
| JP | 2004267097 | A | 9/2004 |
| WO | 0056444 | A2 | 9/2000 |

OTHER PUBLICATIONS

Schwolow, S. et al. Application-Oriented Analysis of Mixing Performance in Microreactors, 2012, Org. Process Res. Dev. 16(9): 1513-1522 (Year: 2012).*

Gutmann, B. et al. Continuous-Flow Technology—A Tool for the Safe Manufacturing of Active Pharmaceutical Ingredients, 2015, Angewandte Chemie International EditionVolume, 54(23): 6653-6939 (Year: 2015).*

Chen, X. et al. Efficient biosynthesis of ethyl (R)-4-chloro-3-hydroxybutyrate using a stereoselective carbonyl reductase from Burkholderia gladioli, 2016, BMC Biotechnology, 16(70): 1-12 (Year: 2016).*

Teresa Burgahn et al. Evaluation of a Microreactor for Flow Biocatalysis by Combined Theory and Experiment[J]. ChemCatChem, 2020, 12(9).

M.Kitamura et al. A practical asymmetric synthesis of carnitine. Tetrahedron Letters, 1988, 29, 1555-1556.

Aragozzini F et al. Stereoselective reduction of non-cyclic carbonyl compounds by some eumycetes. Applied Microbiology & Biotechnology, 1986, 24(2):175-177.

Bare,G et al. Bioconversion of a L-Carnitin Precursor in a One- or Two-Phase System[J]. Applied Biochemistry & Biotechnology, 1991, 28-29(1):445-456.

Bing-Nan Zhou et al. Stereochemical control of yeast reductions. 1. Asymmetric synthesis of L-carnitine. Journal of the American Chemical Society, 1983, 105, 5925-5926.

Wong C et al. Enzymatic vs. fermentative synthesis: thermostable glucose dehydrogenase catalyzed regeneration of NAD(P)H for use in enzymatic synthesis. Journal of the American Chemical Society, 1985, 107(13):4028-4031.

Li Ti. The application of microreactors in the field of chemistry and chemical engineering[J]. Global Market, 2016, 000 (029):138.

Committee of "Manual of Metrological Testing Technology". Manual of Metrological Testing Technology. vol. 13, Chemistry. China Metrology Press, 1997, p. 129.

* cited by examiner

METHOD FOR THE CONTINUOUS FLOW SYNTHESIS OF (R)-4-HALO-3-HYDROXY-BUTYRATE

REFERENCE TO AN ELECTRONIC SEQUENCE LISTING

The contents of the electronic sequence listing (Name: SequenceListing.txt; Size: 3,232 bytes; and Date of Creation: Jan. 13, 2025) is herein incorporated by reference in its entirety.

CROSS-REFERENCE TO RELATED APPLICATIONS

This application claims the benefit of priority from Chinese Patent Application No. 202011235128.8, filed on Nov. 8, 2020. The content of the aforementioned application, including any intervening amendments thereto, is incorporated herein by reference in its entirety.

TECHNICAL FIELD

This application relates to organic synthesis, and more particularly to a method for the continuous flow synthesis of (R)-4-halo-3-hydroxy-butyrate using a micro-reaction system.

BACKGROUND (R)-4-halo-3-hydroxy-butyrate is a key intermediate for the synthesis of L-carnitine. Considering the atom economy, the (R)-4-halo-3-hydroxy-butyrate is generally prepared via asymmetric catalytic reduction of halogenated acetoacetate. Kitamura et al. (*Tetrahedron Letters*, 1988, 29, 1555-1556) disclosed a method for preparing (R)-4-halo-3-hydroxy-butyrate through an asymmetric reduction of halogenated acetoacetate under the catalysis of a chiral complex formed by the coordination of a chiral bisphosphine ligand BINAP with ruthenium, in which the enantiomeric excess (ee) of (R)-4-halo-3-hydroxy-butyrate reached 97%. Unfortunately, this preparation process is greatly limited by the complicated preparation of the catalyst and its ligand, low substrate/catalyst (S/C) value, high cost, harsh reaction conditions (high temperature and high pressure), complicated operation and high safety risks. Moreover, Chinese Patents Nos. 106947752 and 108018321, U.S. Pat. No. 4,710,468, Aragozzini et al. (*Applied Microbiology and Biotechnology*, 1986, 24, 175-177), Bare et al. (*Applied Biochemistry and Biotechnology*, 1991, 28/29, 445-456), Zhou et al. (*Journal of American Chemical Society*, 1983, 105, 5925-5926) and Wong et al. (*Journal of American Chemical Society*, 1985, 107, 4028-4031) all disclosed a method for preparing ethyl (R)-4-chloro-3-hydroxy-butyrate through enzymatic asymmetric reduction of ethyl chloroacetoacetate. Impressively, this method had advantages of high stereoselectivity, mild reaction conditions and environmental benignity, but it also suffered from long reaction times (up to dozens of hours) and low process efficiencies and yields.

The above-mentioned enzymatic method is essentially a multi-phase reaction, in which the substrate is in the organic phase and the enzyme catalyst and the corresponding coenzyme factors are in the aqueous phase. Hence the apparent reaction rate is closely associated with the inter phase mass transfer process together with the interfacial area and dynamic interfacial behavior. The enzymatic methods were traditionally performed in batch reactors. However, due to the poor multiphase mass transfer and mixing performances as well as the wide droplet size distributions, the batch reactors can significantly affect the reaction processes, led to decreased reaction rates and selectivities. Thus, relatively low yields and efficiencies were obtained in conventional batch approaches. In view of this, there is an urgent need for those skilled in the art to develop a rapid, operationally simple, high-yielding and efficient method for synthesizing (R)-4-halo-3-hydroxy-butyrate to overcome the defects in the existing enzymatic methods.

SUMMARY

In view of the shortcomings in the prior art, this disclosure provides a method for the continuous flow synthesis of (R)-4-halo-3-hydroxy-butyrate using a micro-reaction system with less time consumption, high yield, simple operation and high efficiency.

Technical solutions of this disclosure are described as follows.

This disclosure provides a method for the continuous flow synthesis of (R)-4-halo-3-hydroxy-butyrate using a micro-reaction system, wherein the micro-reaction system comprises a micro-mixer and N micro-reaction units, and N is a positive integer selected from 1-20; each of the N micro-reaction units comprises a micro-channel reactor and a pH regulator that are sequentially connected with each other; an outlet of the micro-mixer is connected with an inlet of a micro-channel reactor in the micro-reaction unit (referred as the first micro-reaction unit hereafter) intimately adjacent to the micro-mixer, and an outlet of the micro-channel reactor in the first micro-reaction unit is connected with a first inlet of a pH regulator in the first micro-reaction unit; a second inlet of the pH regulator in the first micro-reaction unit is configured to allow a pH adjusting agent to be pumped in; an outlet of the pH regulator in the first micro-reaction unit is connected with an inlet of a micro-channel reactor in the next micro-reaction unit; the N micro-reaction units are successively connected in series to form a tandem system of "micro-channel reactor—pH regulator—micro-channel reactor—pH regulator . . . micro-channel reactor—pH regulator" wherein the micro-channel reactors and pH regulators are connected alternately; the micro-reaction system further comprises a pH regulating system consisting of a pH meter, a computer, at least N pumps for transporting the pH adjusting agent and a tank for storing the pH adjusting agent; the pH meter comprises a main body and at least N pH-measuring probes; the pH-measuring probes are separately fixed in each pH regulator in order to measure the pH of the reaction mixture in each pH regulator; the main body of the pH meter is simultaneously connected to all the pH-measuring probes and the computer; the computer is connected to all the pumps that transport the pH adjusting agent the pumps that transport the pH adjusting agent are simultaneously connected to the pH adjusting agent storing tank and the pH regulators; the computer is configured to monitor the pH of the reaction mixture flowing into each pH regulator, and in the meantime, calculate and control the corresponding flow rate of the pH adjusting agent that is being pumped into each pH regulator in real time by using a software, thereby accurately adjusting the pH of the reaction mixture in all the pH regulators;

wherein the method comprises:
(1) pumping a substrate solution containing halogenated acetoacetate and a biocatalyst solution into the micro-mixer simultaneously to mix the two solutions to obtain a reaction mixture; and (2) allowing the reaction mixture flowing out of the micro-mixer to enter the N micro-reaction units connected in series; and subjecting the reaction mixture to biocatalytic asymmetric reduction reaction; allowing the reaction mixture to flow out of the micro-reaction system through a back pressure valve to enter a receiving flask; and subjecting the reaction mixture to separation and purification to obtain the target product (R)-4-halo-3-hydroxy-butyrate;

wherein the (R)-4-halo-3-hydroxy-butyrate is shown in formula (I), and the halogenated acetoacetate is shown in formula (II); and the biocatalytic asymmetric reduction reaction is shown in the following reaction scheme:

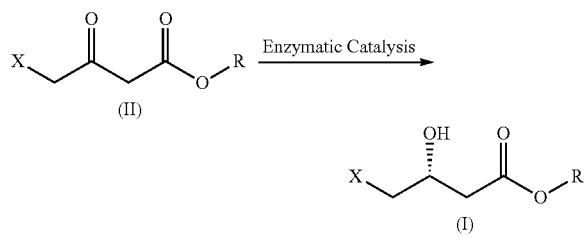

wherein X is halogen selected from F, Cl, Br or I; and R is linear and branched $C_1$-$C_8$ alkyl, $C_3$-$C_8$ cycloalkyl, monosubstituted and polysubstituted aryl, or monosubstituted and polysubstituted aralkyl.

In some embodiments, in step (1), the substrate solution is prepared by dissolving the halogenated acetoacetate in a water-immiscible organic solvent, where the water-immiscible organic solvent is benzene, toluene, ethylbenzene, chlorobenzene, xylene, dichlorobenzene, dichloromethane, chloroform, carbon tetrachloride, dichloroethane, ethyl acetate, pentane, cyclopentane, hexane, cyclohexane, octane or isooctane, preferably toluene or ethylbenzene.

In some embodiments, a concentration of the halogenated acetoacetate in the substrate solution is 0.01-0.80 g/mL.

In some embodiments, in step (1), the biocatalyst solution comprises biocatalyst, glucose, a phosphate and water.

In some embodiments, the biocatalyst is carbonyl reductase YOL151W, a carbonyl reductase YOL151W mutant, a whole cell biocatalyst containing the carbonyl reductase YOL151W, a whole cell biocatalyst containing the carbonyl reductase YOL151W mutant, or a combination thereof.

In some embodiments, a concentration of the biocatalyst in the biocatalyst solution is 0.1-1.3 g/mL.

In some embodiments, a concentration of the glucose in the biocatalyst solution is 0.05-1.5 g/mL.

In some embodiments, the phosphate is a mixture of sodium dihydrogen phosphate and disodium hydrogen phosphate or a mixture of potassium dihydrogen phosphate and disodium hydrogen phosphate.

In some embodiments, the biocatalyst solution has a pH of 6-10, preferably 6.5-7.5.

In some embodiments, in step (1), the flow rates of the substrate solution and the biocatalyst solution pumped into the micro-mixer are adjusted such that a weight ratio of the biocatalyst to the halogenated acetoacetate entering the micro-mixer is 0.2-2:1, preferably 0.5-1.5:1.

In some embodiments, the temperature in the micro-mixer is controlled at 10° C.-50° C., preferably 25° C.-45° C.

In some embodiments, in step (2), each of the micro-reaction units consists of a micro-channel reactor and a pH regulator that are sequentially connected with each other; the pH regulator is a container equipped with a magnetic stir bar or at least an impeller that can efficiently agitate the reaction mixture inside to a desirable degree of mixing in a short time; and the effective internal volume of the pH regulator is 20-70% that of the micro-channel reactor in the same micro-reaction unit, and preferably 30-60% that of the micro-channel reactor in the same micro-reaction unit.

Since the viscosity of the reaction mixture increases with the progression of the reaction, the fluid mobility thus worsens. The reaction mixture may stop flowing when the viscosity increases to a value high enough, hindering the continuous flow synthesis. Therefore, it is important to ensure that the pH regulator is equipped with a magnetic stir bar or at least an impeller that can provide a desirable degree of mixing to the reaction mixture inside. Due to the shear thinning behavior of the reaction mixture, the fluid viscosity decreases with increasing shear stress. Accordingly, the shear stress imposed by the agitation in the pH regulator can decrease the viscosity of the reaction mixture, thereby promoting the fluid mobility. On the other hand, the pumping of the pH adjusting agent into the pH regulators can not only adjust the pH of the reaction mixture inside, but also dilute the concentration of the reactants, thereby increasing the fluid mobility as well. The effective internal volume of the pH regulator should be 20-70%, and preferably 30-60% that of the micro-channel reactor in the same micro-reaction unit in order to achieve a relatively uniform distribution of the shear force exerted by the agitator (i.e., magnetic stir bar or impeller), thereby enabling a desirable degree of mixing and maintaining fluid flow at a satisfactory level.

In some embodiments, the pH regulating system is configured to adjust the pH of the reaction mixture in each pH regulator to 6-10, preferably 6.5-7.5.

In some embodiments, the pH adjusting agent is an aqueous solution of an inorganic base.

In some embodiments, the inorganic base is an alkali metal carbonate, an alkali metal hydroxide, or a combination thereof. In an embodiment, the inorganic base is selected from lithium carbonate, sodium carbonate, potassium carbonate, lithium bicarbonate, sodium bicarbonate, potassium bicarbonate, lithium hydroxide, sodium hydroxide, potassium hydroxide or a combination thereof.

In some embodiments, the aqueous solution of the inorganic base comprises 3-40 wt %, preferably 5-30 wt % of the inorganic base.

In some embodiments, in step (2), the temperature of the micro-channel reactor of each of the micro-reaction units is controlled to be 10-50° C., preferably 25-45° C.

In some embodiments, in step (2), the temperature in the pH regulator of each of the micro-reaction units is controlled to be 10-50° C., preferably 25-45° C.

In some embodiments, in step (2), the residence time of the reaction mixture in the micro-channel reactor of each of the micro-reaction units is 0.1-30 min.

In some embodiments, in step (2), the residence time of the reaction mixture in the pH regulator of each of the micro-reaction units is 0.1-30 min.

In some embodiments, in step (2), the micro-reaction unit intimately adjacent to the back pressure valve is connected to the back pressure valve, and a back pressure of the back pressure valve is 0.1-3 MPa.

In some embodiments, the micro-mixer comprises a first liquid inlet channel and a second liquid inlet channel parallel to each other; one end of the first liquid inlet channel is provided with a first liquid inlet, and the other end of the first liquid inlet channel is closed; one end of the second liquid inlet channel is provided with a second liquid inlet, and the other end of the second liquid inlet channel is provided with a liquid outlet; the first liquid inlet and the second liquid inlet are arranged at the same end; a wall is shared by the first liquid inlet channel and the second liquid inlet channel, and a plurality of micro pores are provided at the common wall to connect the first liquid inlet channel with the second liquid inlet channel; in step (1), the substrate solution is pumped into the first liquid inlet channel, and the biocatalyst solution is pumped into the second liquid inlet channel; and the substrate solution in the first liquid inlet channel flows rapidly through the micro pores into the second liquid inlet channel, and then mixes with the biocatalyst solution in the second liquid inlet channel.

It is import to ensure that the first liquid inlet channel is directly connected to the second liquid inlet channel via the micro pores at the common wall, which enables fast and highly-efficient mixing of the fluid coming from the first liquid inlet channel with the fluid in the second liquid inlet channel.

In some embodiments, the micro pores are circular.

In some embodiments, a hydraulic diameter of each of the micro pores is 0.1-300 μm, preferably 0.2-250 μm, and a distance between two adjacent micro pores is 0.1 μm-1.5 mm, preferably 0.2 μm-1.4 mm.

In some embodiments, the ratio of the total area of the cross-sections of all the micro pores to the area of the common wall is 1%-70%, preferably 2%-65%.

In some embodiments, a cross section of the first liquid inlet channel is circular or rectangular, and a cross section of the second liquid inlet channel is circular or rectangular.

In some embodiments, a hydraulic diameter of the first liquid inlet channel is 0.01-20 mm, preferably 0.02-15 mm, and a hydraulic diameter of the second liquid inlet channel is 0.01-20 mm, preferably 0.02-15 mm.

In some embodiments, a ratio of the hydraulic diameter of each of the p micro pores to the hydraulic diameter of the second liquid inlet channel is 0.0001-0.1:1, preferably 0.0375-0.1:1.

In some embodiments, a length of the first liquid inlet channel is 2-30 mm, preferably 3-28 mm, and a length of the second liquid inlet channel is 4-100 mm, preferably 5-80 mm.

In some embodiments, the micro-channel reactor is a tubular micro-channel reactor or a plate-type micro-channel reactor.

In some embodiments, an inner diameter of the tubular micro-channel reactor is 100 μm-10 mm, preferably 120 μm-5.35 mm.

In some embodiments, a hydraulic diameter of a reaction fluid channel of the plate-type micro-channel reactor is 100 μm-10 mm, preferably 120 μm-5.35 mm.

Compared to the methods carried out in a traditional batch reactor, the method provided herein for the continuous flow synthesis of (R)-4-halo-3-hydroxy-butyrate using a micro-reaction system has the following beneficial effects.

1. Due to the excellent mass transfer and molecular mixing performances of the micro-channel reactor, the reaction time of the enzymatic asymmetric reduction of the halogenated acetoacetate is considerably shortened. To our surprise, the reaction can be completed in just a few minutes compared to the fact that dozens of hours were required in traditional batch reactors. Moreover, the side reactions are significantly inhibited in the continuous flow synthesis, leading to higher yields of (R)-4-halo-3-hydroxy-butyrate.

2. The pH of the reaction mixture is constantly adjusted while flowing through the pH regulators that are connected to the micro-channel reactors during the continuous flow reaction process. The computer reads the pH values of the reaction mixture in the pH regulators measured by the pH meter in real time, which enables automatic adjustment and control of the flow rates of the pH adjusting agent that is being pumped into the pH regulators so that the pH of the reaction mixture in the pH regulators can be accurately controlled in real-time. The method provided herein not only has a high degree of automation, but also can accurately control the pH of the reaction mixture during the continuous flow reaction process, thus further improving the yield of the target product.

3. The computer can monitor the pH variation of the reaction mixture in the pH regulators in real-time during the continuous flow reaction process, which enables precise control of the flow rates of the pH adjusting agent that is being pumped into the pH regulators, thus avoiding the generation of excessive waste water and significantly reducing the wastewater discharge volumes.

4. The method provided herein enables the continuous flow synthesis of (R)-4-halo-3-hydroxy-butyrate. The process can be run continuously and uninterruptedly without any external intervention. This method has the advantages of simple operation, a high degree of automation and high space-time efficiency, significantly reduced labor intensity and production cost.

So far, the continuous flow synthesis of (R)-4-halo-3-hydroxy-butyrate in a micro-reaction system employing enzymatic asymmetric reduction of halogenated acetoacetate has not been reported in the literature.

Figure 1:
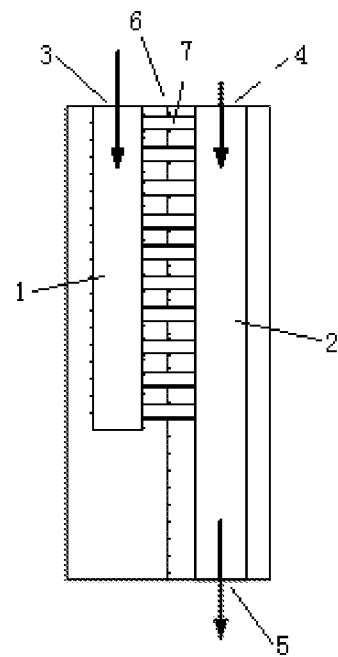
FIG. 1 is a schematic diagram of a micro-mixer in accordance with an embodiment of the disclosure.

In the drawings, 1, first liquid inlet channel; 2, second liquid inlet channel; 3, first liquid inlet; 4, second liquid inlet; 5, liquid outlet; 6, common wall; 7, micro pore; 8, substrate solution transport pump; 9, biocatalyst solution transport pump; 10, micro-mixer; 11, first micro-channel reactor; 12, pH adjusting agent storage tank; 13, first pH adjusting agent transport pump; 14, first pH regulator; 15, first pH-measuring probe; 16, computer; 17, second micro-channel reactor; 18, second pH adjusting agent transport pump; 19, second pH regulator; 20, second pH-measuring probe; 21, pH meter main body; 22, third micro-channel reactor; 23, third pH adjusting agent transport pump; 24, third pH regulator; 25, third pH-measuring probe; 26, back pressure valve; 27, receiving flask; 28, first temperature-control layer; 29, reaction layer; and 30, second temperature-control layer.

DETAILED DESCRIPTION OF EMBODIMENTS

As used herein, term "alkyl" refers to linear or branched $C_1$-$C_{10}$ alkyl, preferably $C_1$-$C_8$ alkyl, and more preferably $C_1$-$C_5$ alkyl, such as methyl, ethyl, n-propyl, isopropyl, n-butyl, isobutyl, sec-butyl, tert-butyl, n-pentyl and n-hexyl.

As used herein, the $C_3$-$C_8$ cycloalkyl includes but is not limited to cyclopropyl, cyclobutyl, cyclopentyl and cyclohexyl.

As used herein, term "aryl" refers to a $C_6$-$C_{36}$, preferably $C_6$-$C_{14}$, monocyclic or polycyclic aryl, such as phenyl, naphthyl, anthryl, phenanthryl, biphenyl, binaphthyl, etc. The aryl may be monosubstituted or polysubstituted aryl, for example, the aryl may carry one or more substituents such as alkyl.

As used herein, term "aralkyl" refers to an alkyl in which at least one hydrogen atom is substituted with an aryl, and preferably a $C_7$-$C_{15}$ aralkyl, such as benzyl, 1-phenethyl, 2-phenylethyl, 1-phenylpropyl, 3-naphthylpropyl, etc. The aryl in the aralkyl may be monosubstituted or polysubstituted aryl, for example, the aryl in the aralkyl may carry one or more substituents such as an alkyl.

As shown in FIG. 1, the micro-mixer used herein includes a first liquid inlet channel 1 and a second liquid inlet channel 2 parallel to each other. One end of the first liquid inlet channel 1 is provided with a first liquid inlet 3, and the other end is closed. One end of the second liquid inlet channel 2 is provided with a second liquid inlet 4, and the other end is provided with a liquid outlet 5. The first liquid inlet 3 and the second liquid inlet 4 are arranged at the same end. A wall 6 is shared by the first liquid inlet channel 1 and the second liquid inlet channel 2, and micro pores 7 are provided at the common wall 6 to connect the first liquid inlet channel 1 with the second liquid inlet channel 2. The liquid in the first liquid inlet channel 1 is able to flow into the second liquid inlet channel 2 rapidly through the micro pores 7, and then mixes with the liquid in the second liquid inlet channel 2.

In some embodiments, the micro pore 7 is circular.

In some embodiments, a plurality of micro pores 7 are provided at the common wall 6 to connect the first liquid inlet channel 1 with the second liquid inlet channel 2. In some embodiments, a hydraulic diameter of each of the micro pores 7 is 0.1-300 μm, preferably 0.2-250 μm, and more preferably 15-40 μm, and a distance between two adjacent micro pores 7 is 0.1 μm-1.5 mm, preferably 0.2 μm-1.4 mm.

In some embodiments, the ratio of the total area of the cross-sections of all the micro pores 7 to the area of the common wall 6 is 1-70%, preferably 2-65%. In some embodiments, a cross section of the first liquid inlet channel 1 is circular or rectangular, and a cross section of the second liquid inlet channel 2 is circular or rectangular.

In some embodiments, a hydraulic diameter of the first liquid inlet channel 1 is 0.01-20 mm, preferably 0.02-15 mm, and a hydraulic diameter of the second liquid inlet channel 2 is 0.01-20 mm, preferably 0.02-15 mm.

In some embodiments, a ratio of the hydraulic diameter of the micro pore 7 to the hydraulic diameter of the second liquid inlet channel 2 is 0.0001-0.1:1, preferably 0.0375-0.1:1.

In some embodiments, a length of the first liquid inlet channel 1 is 2-30 mm, preferably 3-28 mm, and a length of the second liquid inlet channel 2 is 4-100 mm, preferably 5-80 mm.

The micro-mixer is configured to enable the fluid in the first liquid inlet channel 1 to be dispersed into the liquid in the second liquid inlet channel 2 in the form of micro droplets to form a micro dispersion system. Compared with a conventional micro-mixer, the micro-mixer of the disclosure can greatly enhance the liquid-liquid mass transfer process by shortening the mass transfer distance and improving the mass transfer area based on the micro droplets with high dispersibility and high specific surface area. Therefore, the micro-mixer can effectively enhance the liquid-liquid reaction process.

When the micro-mixer shown in FIG. 1 is used, the substrate solution containing halogenated acetoacetate enters the first liquid inlet channel 1 through the first liquid inlet 3, and the biocatalyst solution enters the second liquid inlet channel 2 from the second liquid inlet 4. After filling the first liquid inlet channel 1, the substrate solution is driven to enter the second liquid inlet channel 2 through the micro pores 7 by the pressure, and then forms a micro-droplet dispersion system in the second liquid inlet channel 2 under the shearing of the biocatalyst solution. The resultant micro-droplet dispersion system has an extremely large specific surface area and mass transfer coefficient, which is conducive to the efficient mixing and reaction of the two fluids, shortening the reaction time and improving the yield of (R)-4-halo-3-hydroxy-butyrate.

In order to make the objects, technical solutions and advantages of the invention clearer, the invention will be further described below in detail with reference to the embodiments.

Example 1

Figure 2:
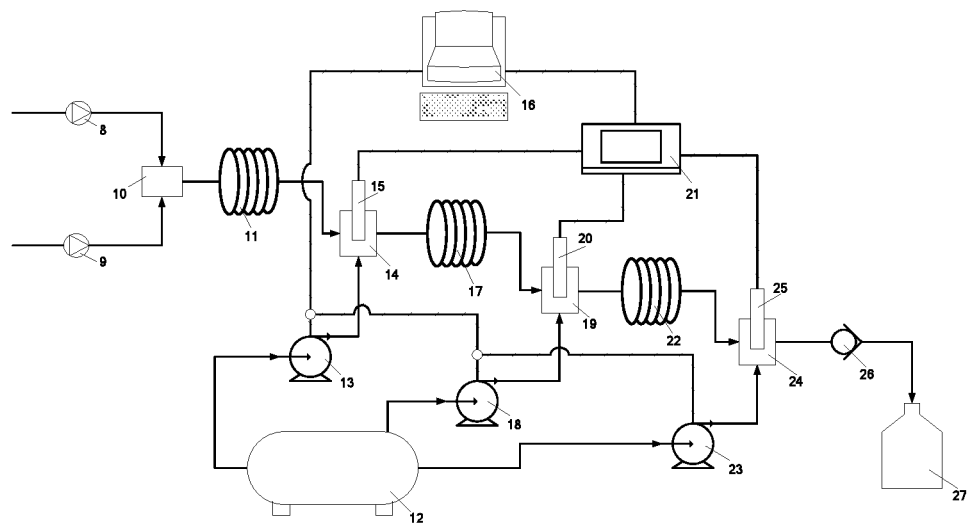
FIG. 2 is a schematic diagram of a micro-reaction system in accordance with an embodiment of the disclosure.

Provided herein was a method for preparing ethyl (R)-4-halo-3-hydroxy-butyrate using a micro-reaction system shown in FIG. 2, where the micro-reaction system included a micro-mixer 10, a first micro-channel reactor 11, a first pH regulator 14, a second micro-channel reactor 17, a second pH regulator 19, a third micro-channel reactor 22, a third pH regulator 24, a back pressure valve 26, a receiving flask 27, a computer 16, a pH meter, a first pH adjusting agent transport pump 13, a second pH adjusting agent transport pump 18, a third pH adjusting agent transport pump 23 and a pH adjusting agent storage tank 12.

The pH meter consisted of a pH meter main body 21, a first pH-measuring probe 15, a second pH-measuring probe 20 and a third pH-measuring probe 25.

The computer 16, the pH meter, the first pH adjusting agent transport pump 13, the second pH adjusting agent transport pump 18, the third pH adjusting agent transport pump 23 and the pH adjusting agent storage tank 12 together constituted an automatic pH regulating system.

The micro-mixer 10 was shown in FIG. 1, of which the structural parameters were presented as follows. The hydraulic diameters of the micro pores 7 in the micro-mixer 10 connecting the first liquid inlet channel 1 with the second liquid inlet channel 2 were 30 μm, and the distance between two adjacent micro pores was 30 μm. The first liquid inlet channel 1 had a rectangular cross section with a length of 600 μm and a width of 300 μm. The first liquid inlet channel 1 had a hydraulic diameter of 400 μm, and a length of 10 mm. The second liquid inlet channel 2 had a rectangular cross section with a length of 600 μm and a width of 300 μm. The second liquid inlet channel 2 had a hydraulic diameter of 400 μm and a length of 30 mm. The ratio of the total area of the cross-sections of all the micro pores 7 to the area of the common wall 6 was 30%.

The first micro-channel reactor 11, the second micro-channel reactor 17 and the third micro-channel reactor 22 all were a tubular micro-channel reactor made of 316 L stainless steel, and had an outer diameter of 1.6 mm, an inner diameter of 0.6 mm, and a total volume of 7 mL. The temperature of the first micro-channel reactor 11, the second micro-channel reactor 17 and the third micro-channel reactor 22 was adjusted and controlled by a thermostatic oil bath.

The first pH regulator 14, the second pH regulator 19, and the third pH regulator 24 had the same structure, in which a magnetic stir bar was provided for mixing the liquid materials. The volume of the pH regulator 14 was 42% of the reaction volume of the first micro-channel reactor 11. The volume of the pH regulator 19 was 42% of the reaction volume of the second micro-channel reactor 17. The volume of the pH regulator 24 was 42% of the reaction volume of the third micro-channel reactor 22.

The substrate solution transport pump 8 was configured to pump the substrate solution into the first liquid inlet channel 1 of the micro-mixer 10, and the biocatalyst solution transport pump 9 was configured to pump the biocatalyst solution into the second liquid inlet channel 2 of the micro-mixer 10.

The first pH-measuring probe 15, the second pH-measuring probe 20 and the third pH-measuring probe 25 were fixed inside the first pH regulator 14, the second pH regulator 19 and the third pH regulator 24, respectively. The pH meter main body 21 was connected to the first pH-measuring probe 15, the second pH-measuring probe 20, the third pH-measuring probe 25 and the computer 16, respectively. The computer 16 monitored the pH of the reaction mixture flowing into the first pH regulator 14, the second pH regulator 19 and the third pH regulator 24, and calculated and accurately controlled the flow rates of the pH adjusting agent pumped into the above three pH regulators in real time by using a software. The first pH adjusting agent transport pump 13, the second pH adjusting agent transport pump 18 and the third pH adjusting agent transport pump 23 were configured to pump the pH adjusting agent into the first pH regulator 14, the second pH regulator 19 and the third pH regulator 24, respectively. The storage tank 12 was configured to store the pH adjusting agent, which was a 20 wt % $K_2CO_3$ aqueous solution. The pH of the reaction mixture in the above-mentioned three pH regulators can be adjusted to 6-10 by using this automatic pH regulating system.

The method was specifically described as follows.

(1) Ethyl chloroacetoacetate was dissolved in toluene to a concentration of 0.20 g/mL to prepare a substrate solution. Sodium dihydrogen phosphate and disodium hydrogen phosphate were dissolved in water to prepare a 100 mmol/L phosphate buffered solution (pH 6.7), to which glucose and a whole cell catalyst containing a carbonyl reductase YOL151W mutant were added to concentrations of 0.44 g/mL and 0.4 g/mL, respectively, to obtain a biocatalyst solution. A 20 wt % $K_2CO_3$ aqueous solution was prepared as the pH adjusting agent and stored in the pH adjusting agent storage tank 12.

(2) The substrate solution and the biocatalyst solution prepared in step (1) were pumped into the micro-mixer 10 simultaneously at the same flow rate of 1.86 mL/min; the two solutions were mixed in the micro-mixer 10 to obtained a reaction mixture.

(3) The reaction mixture flowing out of the micro-mixer 10 sequentially entered the first micro-channel reactor 11, the first pH regulator 14, the second micro-channel reactor 17, the second pH regulator 19, the third micro-channel reactor 22, and the third pH regulator 24 to enable a biocatalytic asymmetric reduction reaction. Then the reaction mixture flowed into the receiving flask 27 through the back pressure valve 26, and was subjected to separation and purification to obtain the target product ethyl (R)-4-halo-3-hydroxy-butyrate. The temperatures of the first micro-channel reactor 11, the first pH regulator 14, the second micro-channel reactor 17, the second pH regulator 19, the third micro-channel reactor 22 and the third pH regulator 24 were all controlled at 30° C., and the back pressure of the back pressure valve 26 was set at 0.3 MPa. The residence time of the reaction mixture from entering the micro-mixer 10 to enter the receiving flask 27 was 8 min. The pH of the reaction mixture in the first pH regulator 14, the second pH regulator 19 and the third pH regulator 24 was accurately controlled at 6.7 by using the automatic pH regulating system.

The resultant reaction mixture was sampled and quantitatively analyzed by HPLC (Agilent) based on peak area. The results showed that the substrate ethyl chloroacetoacetate reached a complete conversion, and the target product ethyl (R)-4-halo-3-hydroxy-butyrate had a yield of 96.8%.

Reference can be made to Chinese Patent Application Publication No. 111172124A for the preparation of the whole cell catalyst containing the carbonyl reductase YOL151W mutant. Thus, the carbonyl reductase YOL151W mutant has the amino acid sequence of SEQ ID NO: 1.

Example 2

This example was basically the same as Example 1 with respect to the micro-reaction system and experimental operations and conditions except that in this example, the pH of the reaction mixture in the first pH regulator 14, the second pH regulator 19 and the third pH regulator 24 was accurately controlled at 7.0 by using the automatic pH regulating system.

The resultant reaction mixture was quantitatively analyzed by HPLC (Agilent) based on peak area. The results showed that the substrate ethyl chloroacetoacetate reached a complete conversion, and the target product ethyl (R)-4-halo-3-hydroxy-butyrate had a yield of 98.7%.

Example 3

This example was basically the same as Example 1 with respect to the micro-reaction system and experimental operations and conditions except that in this example, the pH of the reaction mixture in the first pH regulator 14, the second pH regulator 19 and the third pH regulator 24 was accurately controlled at 6.2 by using the automatic pH regulating system.

The resultant reaction mixture was quantitatively analyzed by HPLC (Agilent) based on peak area. The results demonstrated that the substrate ethyl chloroacetoacetate reached a complete conversion, and the target product ethyl (R)-4-halo-3-hydroxy-butyrate had a yield of 95.4%.

Example 4

This example was basically the same as Example 1 with respect to the micro-reaction system and experimental operations and conditions except that in this example, the pH of the reaction mixture in the first pH regulator 14, the second pH regulator 19 and the third pH regulator 24 was accurately controlled at 7.3 by using the automatic pH regulating system.

The resultant reaction mixture was quantitatively analyzed by HPLC (Agilent) based on peak area. The results showed that the substrate ethyl chloroacetoacetate reached a complete conversion, and the target product ethyl (R)-4-halo-3-hydroxy-butyrate had a yield of 98.5%.

Example 5

This example was basically the same as Example 1 with respect to the micro-reaction system and experimental operations and conditions except that in this example, the pH of the reaction mixture in the first pH regulator 14, the second pH regulator 19 and the third pH regulator 24 was accurately controlled at 8.0 by using the automatic pH regulating system.

The resultant reaction mixture was quantitatively analyzed by HPLC (Agilent) based on peak area. The results showed that the substrate ethyl chloroacetoacetate reached a complete conversion, and the target product ethyl (R)-4-halo-3-hydroxy-butyrate had a yield of 95.1%.

Example 6

The micro-reaction system used herein was shown in FIG. 2, in which the first micro-channel reactor 11, the second micro-channel reactor 17, the third micro-channel reactor 22 were polytetrafluoroethylene (PTFE) tubular micro-channel reactors having an outer diameter of 1.6 mm, an inner diameter of 0.6 mm and a volume of 7 mL. All the other experimental operations and conditions were the same as those in Example 1. The resultant reaction mixture was quantitatively analyzed by HPLC (Agilent) based on peak area. The results showed that the substrate ethyl chloroacetoacetate reached a complete conversion, and the target product ethyl (R)-4-halo-3-hydroxy-butyrate had a yield of 96.5%.

Example 7

The micro-reaction system used herein was shown in FIG. 2, in which the first micro-channel reactor 11, the second micro-channel reactor 17, the third micro-channel reactor 22 were polyetheretherketone (PEEK) tubular micro-channel reactors having an outer diameter of 1.6 mm, an inner diameter of 0.6 mm and a volume of 7 mL. All the other experimental operations and conditions were the same as those in Example 1.

The resultant reaction mixture was quantitatively analyzed by HPLC (Agilent) based on peak area. The results showed that the substrate ethyl chloroacetoacetate reached a complete conversion, and the target product ethyl (R)-4-halo-3-hydroxy-butyrate had a yield of 96.4%.

Example 8

Figure 3:
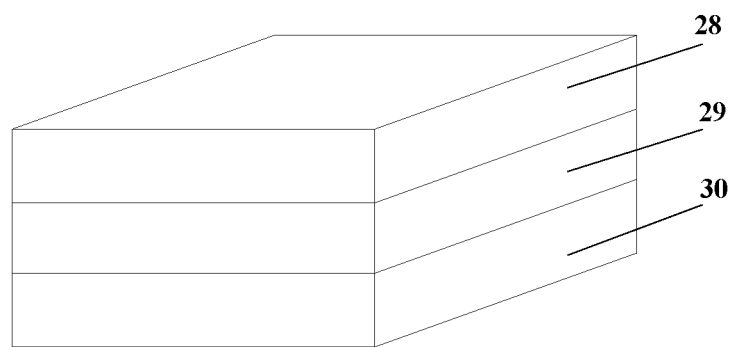
FIG. 3 is a schematic diagram of a plate-type micro-channel reactor in accordance with an embodiment of the disclosure.

The micro-reaction system used herein was shown in FIG. 2, in which the first micro-channel reactor 11, the second micro-channel reactor 17, the third micro-channel reactor 22 were plate-type micro-channel reactors made of 316 L stainless steel as shown in FIG. 3. The three plate-type micro-channel reactors all had a cuboid structure with a length of 12 cm, a width of 10 cm and a height of 3 cm. The plate-type micro-channel reactor included a first temperature-control layer 28, a reaction layer 29 and a second temperature-control layer 30 from top to bottom. The first temperature-control layer 28 and the second temperature-control layer 30 were used to adjust and control the temperature of the reaction layer 29. The reaction layer 29 was provided with a reaction fluid channel with a cross section of 400 μm (width)×600 μm (length), a hydraulic diameter of 480 μm, and a total volume of 7 mL. All the other experimental operations and conditions were the same as those in Example 1. The resultant reaction mixture was quantitatively analyzed by HPLC (Agilent) based on peak area. The results showed that the substrate ethyl chloroacetoacetate reached a complete conversion, and the target product ethyl (R)-4-halo-3-hydroxy-butyrate had a yield of 96.3%.

Example 9

Provided herein was a method for the continuous flow synthesis of ethyl (R)-4-halo-3-hydroxy-butyrate using a micro-reaction system, which was basically the same as that in Example 1, except that in this example, the hydraulic diameters of the micro pores 7 in the micro-mixer 10 were 15 μm.

The resultant reaction mixture was quantitatively analyzed by HPLC (Agilent) based on peak area. The results showed that the substrate ethyl chloroacetoacetate reached a complete conversion, and the target product ethyl (R)-4-halo-3-hydroxy-butyrate had a yield of 98.2%.

Example 10

Provided herein was a method for the continuous flow synthesis of ethyl (R)-4-halo-3-hydroxy-butyrate using a micro-reaction system, which was basically the same as that in Example 1, except that the hydraulic diameters of the micro pores 7 in the micro-mixer 10 were 40 μm.

The resultant reaction mixture was quantitatively analyzed by HPLC (Agilent) based on peak area. The results showed that the substrate ethyl chloroacetoacetate reached a complete conversion, and the target product ethyl (R)-4-halo-3-hydroxy-butyrate had a yield of 96.3%.

Example 11

Provided herein was a method for the continuous flow synthesis of ethyl (R)-4-halo-3-hydroxy-butyrate using a micro-reaction system, which was basically the same as that in Example 1, except that the hydraulic diameters of the micro pores 7 in the micro-mixer 10 were 150 μm.

The resultant reaction mixture was quantitatively analyzed by HPLC (Agilent) based on peak area. The results showed that the substrate ethyl chloroacetoacetate reached a complete conversion, and the target product ethyl (R)-4-halo-3-hydroxy-butyrate had a yield of 88.2%.

Comparative Example

Provided herein was the traditional method for preparing ethyl (R)-4-halo-3-hydroxy-butyrate using a batch reactor, which was specifically described as follows. (1) Ethyl chloroacetoacetate was dissolved in toluene to obtain a substrate solution (0.20 g/mL). A 100 mmol/L phosphate buffered solution (pH 6.7) was prepared to which glucose and a whole cell catalyst containing a carbonyl reductase YOL151W mutant were added to concentrations of 0.44 g/mL and 0.4 g/mL, respectively, to obtain a biocatalyst solution. A 20 wt % $K_2CO_3$ aqueous solution was prepared as the pH adjusting agent.

(2) 150 mL of the substrate solution and 150 mL of the biocatalyst solution prepared in step (1) were added into the batch reactor, and reacted at 30° C. During the reaction, the pH of the reaction mixture in the batch reactor was continuously monitored, and the $K_2CO_3$ aqueous solution was added dropwise every 3-5 min to keep the pH value of the reaction mixture stable at 6.7.

The reaction mixture was regularly sampled for analysis, and the results showed that the substrate ethyl chloroacetoacetate achieved a conversion of about 35% after 1 h; about 52% after 2 h; about 64% after 3 h; and about 97% after 8 h, and after 8 hours, the product ethyl (R)-4-halo-3-hydroxy-butyrate achieved a yield of 86%.

The Comparative Example and Example 1 had the same weight ratio of the substrate ethyl chloroacetoacetate to the biocatalyst. Compared to the batch reactor, the continuous flow method employing the micro-reaction system provided herein can considerably shorten the reaction time, greatly suppress the side reactions, and significantly improve the yield of the target product ethyl (R)-4-halo-3-hydroxy-butyrate.

It should be noted that described above are merely preferred embodiments of the invention, which are not intended to limit the invention. It should be understood that any modification, change and replacement made by those skilled in the art without departing from the spirit of the invention should fall within the scope of the invention defined by the appended claim.

What is claimed is:

1. A method for the continuous flow synthesis of (R)-4-halo-3-hydroxy-butyrate using a micro-reaction system, wherein the micro-reaction system comprises a micro-mixer and N micro-reaction units, and N is a positive integer selected from 1-20; each of the N micro-reaction units comprises a micro-channel reactor and a pH regulator that are sequentially connected with each other; an outlet of the micro-mixer is connected with an inlet of a micro-channel reactor in the first micro-reaction unit adjacent to the micro-mixer, and an outlet of the micro-channel reactor in the first micro-reaction unit is connected with a first inlet of a pH regulator in the first micro-reaction unit; a second inlet of the pH regulator in the first micro-reaction unit is configured to allow a pH adjusting agent to be pumped in; an outlet of the pH regulator in the first micro-reaction unit is connected with an inlet of a micro-channel reactor in the next micro-reaction unit so the N micro-reaction units are successively connected in series, and the micro-channel reactors and pH regulators are connected alternately; wherein the micro-reaction system further comprises a pH regulating system consisting of a pH meter, a computer, at least N pumps for transporting the pH adjusting agent and a tank for storing the pH adjusting agent; the pH meter comprises a main body and at least N pH-measuring probes; the pH-measuring probes are separately fixed in each pH regulator in order to measure the pH of the reaction mixture in each pH regulator; the main body of the pH meter is simultaneously connected to all the pH-measuring probes and the computer; the computer is connected to all the pumps that transport the pH adjusting agent; the pumps that transport the pH adjusting agent are simultaneously connected to the pH adjusting agent storing tank and the pH regulators; the computer is configured to monitor the pH of the reaction mixture flowing into each pH regulator, and calculate and control the corresponding flow rate of the pH adjusting agent that is being pumped into each pH regulator in real time by using a software, thereby accurately adjusting the pH of the reaction mixture in all the pH regulators;

the method comprising:
(1) pumping a substrate solution containing ethyl chloroacetoacetate and a biocatalyst solution into the micro-mixer to mix the two solutions to obtain a reaction mixture; and
(2) allowing the reaction mixture to flow out of the micro-mixer to enter the N micro-reaction units connected in series; subjecting the reaction mixture to biocatalytic asymmetric reduction reaction; allowing the reaction mixture to flow out of the micro-reaction system through a back pressure valve to enter a receiving flask; and subjecting the reaction mixture to separation and purification to obtain the target product (R)-4-halo-3-hydroxy-butyrate;

wherein the (R)-4-halo-3-hydroxy-butyrate is shown in formula (I), and the ethyl chloroacetoacetate is shown in formula (II); and the biocatalytic asymmetric reduction reaction is shown in the following reaction scheme:

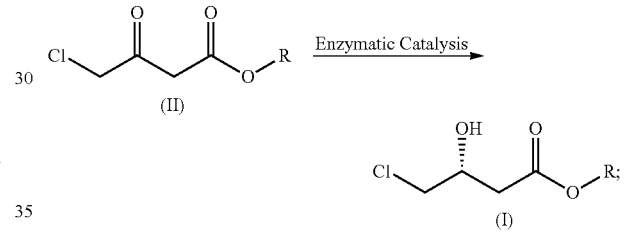

wherein R is linear $C_1$-$C_8$ alkyl, branched $C_1$-$C_8$ alkyl, $C_3$-$C_8$ cycloalkyl, monosubstituted aryl, polysubstituted aryl, monosubstituted aralkyl, or polysubstituted aralkyl.

2. The method of claim 1, wherein in step (1), the substrate solution is prepared by dissolving the ethyl chloroacetoacetate in a water-immiscible organic solvent, wherein the water-immiscible organic solvent is benzene, toluene, ethylbenzene, chlorobenzene, xylene, dichlorobenzene, dichloromethane, chloroform, carbon tetrachloride, dichloroethane, ethyl acetate, pentane, cyclopentane, hexane, cyclohexane, octane or isooctane; and the concentration of the ethyl chloroacetoacetate in the substrate solution is 0.01-0.80 g/mL.

3. The method of claim 2, wherein in step (1), the biocatalyst solution comprises a biocatalyst, glucose, a phosphate and water; wherein the biocatalyst is carbonyl reductase YOL151W, a carbonyl reductase YOL151W mutant, a whole cell biocatalyst containing the carbonyl reductase YOL151W, a whole cell biocatalyst containing the carbonyl reductase YOL151W mutant, or a combination thereof; wherein a concentration of the biocatalyst is 0.1-1.3 g/mL, and a concentration of the glucose is 0.05-1.5 g/mL; wherein the phosphate is a mixture of sodium dihydrogen phosphate and disodium hydrogen phosphate or a mixture of potassium dihydrogen phosphate and disodium hydrogen phosphate; and the biocatalyst solution has a pH of 6-10; and wherein the amino acid sequence of the carbonyl reductase YOL151W mutant is SEQ ID NO: 1.

4. The method of claim 3, wherein in step (1), the flow rates of the substrate solution and the biocatalyst solution pumped into the micro-mixer are adjusted such that a weight ratio of the biocatalyst to the ethyl chloroacetoacetate entering the micro-mixer is 0.2-2:1; and the temperature in the micro-mixer is controlled at 10° C.-50° C.

5. The method of claim 4, wherein the pH regulating system is configured to adjust the pH of the reaction mixture in each pH regulator to 6-10; and the pH adjusting agent is an aqueous solution of an inorganic base.

6. The method of claim 5, wherein the aqueous solution of the inorganic base comprises 3-40 wt % of the inorganic base.

7. The method of claim 6, wherein in step (2), the temperature of the micro-channel reactor of each of the micro-reaction units is controlled at 10-50° C.; the temperature of the pH regulator of each of the micro-reaction units is controlled at 10-50° C.; the residence time of the reaction mixture in the micro-channel reactor of each of the micro-reaction units is 0.1-30 min; and the residence time of the reaction mixture in the pH regulator of each of the micro-reaction units is 0.1-30 min.

8. The method of claim 1, wherein the micro-mixer comprises a first liquid inlet channel and a second liquid inlet channel parallel to each other; one end of the first liquid inlet channel is provided with an opening, and the other end is closed; one end of the second liquid inlet channel is provided with an opening and the other end of the second liquid inlet channel is provided with an outlet; wherein the first liquid inlet opening and the second liquid inlet opening are arranged at the same end; a wall is shared by the first liquid inlet channel and the second liquid inlet channel, and a plurality of micro pores are provided at the common wall to connect the first liquid inlet channel with the second liquid inlet channel;

in step (1), the substrate solution is pumped into the first liquid inlet channel, and the biocatalyst solution is pumped into the second liquid inlet channel; the substrate solution in the first liquid inlet channel flows through the micro pores into the second liquid inlet channel, and then mixes with the biocatalyst solution in the second liquid inlet channel.

9. The method of claim 8, wherein the micro pores are circular;

a hydraulic diameter of each of the micro pores is 0.1-300 μm, and a distance between two adjacent micro pores is 0.1 μm-1.5 mm;

a cross section of the first liquid inlet channel is circular or rectangular, and a cross section of the second liquid inlet channel is circular or rectangular;

a hydraulic diameter of the first liquid inlet channel is 0.01-20 mm, and a hydraulic diameter of the second liquid inlet channel is 0.01-20 mm;

a ratio of the hydraulic diameter of each of the micro pores to the hydraulic diameter of the second liquid inlet channel is 0.0001-0.1:1; and a length of the first liquid inlet channel is 2-30 mm, and a length of the second liquid inlet channel is 4-100 mm.

10. The method of claim 9, wherein the micro-channel reactor of each of the micro-reaction units is a tubular micro-channel reactor or a plate-type micro-channel reactor;

an inner diameter of the tubular micro-channel reactor is 100 μm-10 mm; and a hydraulic diameter of a reaction fluid channel of the plate-type micro-channel reactor is 100 μm-10 mm.

\* \* \* \* \*

SEQUENCE LISTING

```
<160> NUMBER OF SEQ ID NOS: 1

<210> SEQ ID NO 1
<211> LENGTH: 342
<212> TYPE: PRT
<213> ORGANISM: Artificial Sequence
<220> FEATURE:
<223> OTHER INFORMATION: synthetic

<400> SEQUENCE: 1

Met Ser Val Phe Val Ser Gly Ala Asn Gly Phe Ile Ala Gln His Ile
1               5                   10                  15

Val Asp Leu Leu Leu Lys Glu Asp Tyr Lys Val Ile Gly Ser Ala Arg
            20                  25                  30

Ser Gln Glu Lys Ala Glu Asn Leu Thr Glu Ala Phe Gly Asn Asn Pro
        35                  40                  45

Lys Phe Ser Met Glu Val Val Pro Asp Ile Ser Lys Leu Asp Ala Phe
    50                  55                  60

Asp His Val Phe Gln Lys His Gly Lys Asp Ile Lys Ile Val Leu His
65                  70                  75                  80

Thr Ala Ser Pro Met Cys Phe Asp Ile Thr Asp Ser Glu Arg Asp Leu
                85                  90                  95

Leu Ile Pro Ala Val Asn Gly Val Lys Gly Ile Leu His Ser Ile Lys
            100                 105                 110

Lys Tyr Ala Ala Asp Ser Val Glu Arg Val Val Leu Thr Ser Ser Tyr
        115                 120                 125

Ala Ala Val Phe Asp Met Ala Lys Glu Asn Asp Lys Ser Leu Thr Phe
    130                 135                 140

Asn Glu Glu Ser Trp Asn Pro Ala Thr Trp Glu Ser Cys Gln Ser Asp
145                 150                 155                 160

Pro Val Asn Ala Tyr Cys Gly Ser Lys Lys Phe Ala Glu Lys Ala Ala
                165                 170                 175

Trp Glu Phe Leu Glu Glu Asn Arg Asp Ser Val Lys Phe Glu Leu Thr
            180                 185                 190

Ala Val Asn Pro Val Tyr Val Phe Gly Pro Gln Met Phe Asp Lys Asp
        195                 200                 205

Val Lys Lys His Leu Asn Thr Ser Cys Glu Leu Val Asn Ser Leu Met
    210                 215                 220

His Leu Ser Pro Glu Asp Lys Ile Pro Glu Leu Phe Gly Gly Tyr Ile
225                 230                 235                 240

Asp Val Arg Asp Val Ala Lys Ala His Leu Val Ala Phe Gln Lys Arg
                245                 250                 255

Glu Thr Ile Gly Gln Arg Leu Ile Val Ser Glu Ala Arg Phe Thr Met
            260                 265                 270
```

```
Gln Asp Val Leu Asp Ile Leu Asn Glu Asp Phe Pro Val Leu Lys Gly
        275                 280                 285

Asn Ile Pro Val Gly Lys Pro Gly Ser Gly Ala Thr His Asn Thr Leu
    290                 295                 300

Gly Ala Thr Leu Asp Asn Lys Lys Ser Lys Lys Leu Leu Gly Phe Lys
305                 310                 315                 320

Phe Arg Asn Leu Lys Glu Thr Ile Asp Asp Thr Ala Ser Gln Ile Leu
                325                 330                 335

Lys Phe Glu Gly Arg Ile
                340
```